(12) United States Patent
Bell et al.

(10) Patent No.: US 7,591,197 B2
(45) Date of Patent: Sep. 22, 2009

(54) BIOBRIEFCASE AEROSOL COLLECTOR

(75) Inventors: Perry M. Bell, Tracy, CA (US); Allen T. Christian, Madison, WI (US); Christopher G. Bailey, Pleasanton, CA (US); Ladona Willis, Manteca, CA (US); Donald A. Masquelier, Tracy, CA (US); Shanavaz L. Nasarabadi, Livermore, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 88 days.

(21) Appl. No.: 11/497,918

(22) Filed: Aug. 1, 2006

(65) Prior Publication Data

US 2007/0107539 A1    May 17, 2007

Related U.S. Application Data

(60) Provisional application No. 60/734,810, filed on Nov. 8, 2005.

(51) Int. Cl.
*G01N 1/22* (2006.01)
(52) U.S. Cl. .................. 73/863.21; 73/863.22
(58) Field of Classification Search .............. 73/863.22, 73/863.21, 863.12
See application file for complete search history.

(56) References Cited

U.S. PATENT DOCUMENTS

| | | | |
|---|---|---|---|
| 5,317,930 A | | 6/1994 | Wedding |
| 5,412,975 A * | | 5/1995 | Raabe et al. ................ 73/28.04 |
| 6,402,817 B1 | | 6/2002 | Bergman |
| 6,520,034 B1 * | | 2/2003 | Masquelier et al. ....... 73/863.21 |
| 6,688,187 B1 * | | 2/2004 | Masquelier .............. 73/863.22 |
| 6,692,553 B2 * | | 2/2004 | Jordan et al. .................. 95/285 |
| 7,503,229 B2 * | | 3/2009 | Bell et al. ................ 73/863.21 |
| 2002/0045246 A1 | | 4/2002 | McMillan et al. |

FOREIGN PATENT DOCUMENTS

WO     WO 02/075279 A1    9/2002

* cited by examiner

*Primary Examiner*—Hezron Williams
*Assistant Examiner*—Mark Shabman
(74) *Attorney, Agent, or Firm*—Eddie E. Scott; John H. Lee

(57) ABSTRACT

A system for sampling air and collecting particles entrained in the air that potentially include bioagents. The system comprises providing a receiving surface, directing a liquid to the receiving surface and producing a liquid surface. Collecting samples of the air and directing the samples of air so that the samples of air with particles entrained in the air impact the liquid surface. The particles potentially including bioagents become captured in the liquid. The air with particles entrained in the air impacts the liquid surface with sufficient velocity to entrain the particles into the liquid but cause minor turbulence. The liquid surface has a surface tension and the collector samples the air and directs the air to the liquid surface so that the air with particles entrained in the air impacts the liquid surface with sufficient velocity to entrain the particles into the liquid, but cause minor turbulence on the surface resulting in insignificant evaporation of the liquid.

10 Claims, 2 Drawing Sheets

BIOBRIEFCASE AEROSOL COLLECTOR

CROSS-REFERENCE TO RELATED APPLICATIONS

This application claims the benefit of U.S. Provisional Patent Application No. 60/734,810 filed Nov. 8, 2005 and titled "Biobriefcase Aerosol Collector." U.S. Provisional Patent Application No. 60/734,810 filed Nov. 8, 2005 and titled "Biobriefcase Aerosol Collector" is incorporated herein by this reference.

Related systems are disclosed in U.S. patent application Ser. No. 11/497,897 filed Aug. 1, 2006 and titled "Biobriefcase Aerosol Collector" and U.S. patent application Ser. No. 11/497,908 filed Aug. 1, 2006 and titled "Biobriefcase Electrostatic Aerosol Collector Heater." U.S. patent application Ser. No. 11/497,897 filed Aug. 1, 2006 and titled "Biobriefcase Aerosol Collector" and U.S. patent application Ser. No. 11/497,908 filed Aug. 1, 2006 and titled "Biobriefcase Electrostatic Aerosol Collector Heater" are incorporated herein by this reference.

The United States Government has rights in this invention pursuant to Contract No. W-7405-ENG-48 between the United States Department of Energy and the University of California for the operation of Lawrence Livermore National Laboratory.

BACKGROUND

1. Field of Endeavor

The present invention relates to sampling and more particularly to aerosol sampling.

2. State of Technology

U.S. Pat. No. 6,688,187 issued Feb. 10, 2004 to Donald A. Masquelier for "An Aerosol Sampling System" provides the following state of technology information, "As the threat of biological weapons (BW) increases, both in military theaters and civilian populations, the need for complete systems for the rapid detection and analysis of pathogenic organisms becomes increasingly important. The first step in any system for detection and characterization of biological agents is a sample collector. This can take on the simple form of a cotton swab for solid surfaces, or as in the case of airborne pathogens, an aerosol sample collector is used to collect and concentrate airborne particulate into a liquid sample volume for subsequent preparation and analysis. An aerosol sampler is the most appropriate for continuous monitoring scenarios, where repeated swabbing of settled particles is impractical. Aerosol sampling systems also have use in medical facilities and research and development facilities. There are a variety of medical applications where monitoring for biological pathogens would be useful. A good example of this is monitoring in hospitals and clinics for highly infectious agents such as tuberculosis or nosocomial diseases that can threaten the well being of patients and health care professionals. Aerosol sampling systems also have use in environmental monitoring, that is any application that would benefit from environmental monitoring of biological species. One example is continuous aerosol monitoring of bacterial and other pathogens that could affect the health of livestock (such as the recent hoof and mouth disease outbreak)."

U.S. Pat. No. 6,520,034 issued Feb. 18, 2005 to Donald A. Masquelier et al for a "High Air Volume to Low Liquid Volume Aerosol Collector" provides the following state of technology information, "The first step in any system for detection and characterization of biological agents is a sample collector. This can take on the simple form of a cotton swab for solid surfaces, or as in the case of airborne pathogens, an aerosol sample collector is used to collect and concentrate airborne particulate into a liquid sample volume for subsequent preparation and analysis. An aerosol sampler is the most appropriate for continuous monitoring scenarios, where repeated swabbing of settled particles is impractical. Most commercial samplers now available for field use are large, power consuming, and produce collected sample into large volumes of liquid, typically >10 mL. Emerging miniature detection systems analyze much smaller sample volumes, typically <250 μL. When using the presently available air samplers, the sample volume must be 'sub-sampled,' effectively diluting the sample, resulting in a loss of sensitivity of detection. Thus, there is a need for a collector which will collect particulate at a high airflow and yet utilize a low liquid volume."

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The University of California has operated the Lawrence Livermore National Laboratory continuously since the laboratory's inception in 1952 and has extensive experience and resources in biology, chemistry, engineering, and computations. This gives the University of California and the Lawrence Livermore National Laboratory unique ability to tackle the problems of chemical and biological weapons proliferation and terrorist activities.

In an article titled, "Biodetectors Evolving, Monitoring U.S. Cities," by Sally Cole in the May 2003 issue of *Homeland Security Solutions*, it was reported, "The anthrax letter attacks of 2001, and subsequent deaths of five people, brought home the reality of bioterrorism to Americans and provided a wake-up call for the U.S. government about the need for a method to detect and mitigate the impact of any such future attacks. Long before the anthrax letter attacks, scientists at two of the U.S. Department of Energy's national laboratories, Lawrence Livermore National Laboratory (LLNL) and Los Alamos National Laboratory (LANL), were busy pioneering a 'biodetector' akin to a smoke detector to rapidly detect the criminal use of biological agents. This technology is now expected to play a large role in the U.S. government's recently unveiled homeland security counter-terrorism initiative, Bio-Watch, which is designed to detect airborne bioterrorist attacks on major U.S. cities within hours. Announced back in January, Bio-Watch is a multi-faceted, multi-agency program that involves the U.S. Department of Energy, the Environmental Protection Agency (EPA), and the U.S. Department of Health and Human Services' Centers for Disease Control and Prevention (CDC). Many of the EPA's 3,000 air-quality monitoring stations throughout the country are being adapted with biodetectors to register unusual quantities of a wide range of pathogens that cause diseases that incapacitate and kill, according to the EPA. The nationwide network of environmental monitors and biodetectors, which reportedly will eventually monitor more than 120 U.S. cities, is expected to detect and report a biological attack within 24 hours. Citing security reasons, the EPA declined to disclose further details about the program at this time . . . .

The Autonomous Pathogen Detection System (APDS) is a file-cabinet-sized machine that sucks in air, runs tests, and reports the results itself. APDS integrates a flow cytometer and real-time PCR detector with sample collection, sample preparation, and fluidics to provide a compact, autonomously operating instrument capable of simultaneously detecting multiple pathogens and/or toxins. 'The system is designed for fixed locations,' says Langlois, 'where it continuously monitors air samples and automatically reports the presence of specific biological agents. APDS is targeted for domestic applications in which the public is at high risk of exposure to covert releases of bioagents—subway systems, transportation terminals, large office complexes, and convention centers . . . . APDS provides the ability to measure up to 100 different agents and controls in a single sample,' Langlois says. 'It's being used in public buildings right now.' The latest evolution of the biodetector, APDS-II, uses bead-capture immunoassays and a compact flow cytometer for the simultaneous identification of multiple biological simulants. Laboratory tests have demonstrated the fully autonomous operation of APDS-II for as long as 24 hours."

The term "biobriefcase" used in this patent application is intended to mean any device or system for monitoring airborne biological agents in a compact size. One biobriefcase device or system is described in the Sandia National Laboratories Chem/Bio Programs website as follows: "There is a serious need for broad-spectrum bioagent detection. Toward that end, the BioBriefcase project has been undertaken as a joint collaboration between Sandia and Lawrence Livermore National Laboratory for the Department of Homeland Security. It calls for a broad-spectrum bioagent detector that is briefcase-sized and features dramatically reduced reagent consumption, improved sensitivity and rapid response time. Sample preparation and analysis would be carried out on microfluidic, chip-based modules. The detector will use capillary electrophoresis on Sandia's ChemLab platform with three analysis trains; DNA amplification to identify bacteria and viruses using polymerase chain reaction (PCR); immunoassays to identify bacteria, viruses, toxins; and protein signatures to identify toxins. Serving as an environmental monitor, it should function autonomously to collect and detect samples in a stealthy and easily deployed manner. The BioBriefcase should also be capable of being manned by a minimally trained user to function as a portable laboratory, providing quick turn-around between sample analysis and responsive action."

The present invention provides a system for sampling air and collecting particles entrained in the air. The particles potentially include bioagents. The system comprises a system for sampling air and collecting particles entrained in the air that potentially include bioagents. The system comprises providing a receiving surface, directing a liquid to the receiving surface and producing a liquid surface. Collecting samples of the air and directing the samples of air so that the samples of air with particles entrained in the air impact the liquid surface. The particles potentially including bioagents become captured in the liquid. The air with particles entrained in the air impacts the liquid surface with sufficient velocity to entrain the particles into the liquid but cause minor turbulence. The liquid surface has a surface tension and the collector samples the air and directs the air to the liquid surface so that the air with particles entrained in the air impacts the liquid surface with sufficient velocity to entrain the particles into the liquid, but cause minor turbulence on the surface resulting in insignificant evaporation of the liquid.

In one embodiment, the present invention provides an apparatus for sampling air, collecting particles entrained in the air wherein the particles potentially including bioagents, and capturing the particles in a liquid comprising a receiving surface, a liquid input that directs the liquid to the receiving surface and produces a liquid surface, a collector that samples the air and directs the air so that the air with particles entrained in the air impacts the liquid surface, wherein the particles potentially including bioagents become captured in the liquid. In one embodiment, the receiving surface is a bowl receiving surface. One embodiment includes a cone having a forcing cone surface and the forcing cone surface is positioned adjacent the receiving surface. One embodiment includes a cone having a forcing cone surface and contacts for fluid level control on the forcing cone surface, wherein the forcing cone surface is positioned adjacent the receiving surface.

Organisms that can be collected by the present invention include protein toxins, bacteria, viruses, and chemicals. The present invention can be used to limit or prevent civilian exposure to biological pathogens, and initiate early treatment for those exposed; thereby decreasing mortality and morbidity from bioterrorism events. The present invention also has use in medical facilities and research and development facilities. There are a variety of medical applications where monitoring for biological pathogens is useful. A good example of this is monitoring in hospitals and clinics for highly infectious agents such as tuberculosis or nosocomial diseases that can threaten the well being of patients and health care professionals. The present invention also has use in environmental monitoring, that is any application that would benefit from environmental monitoring of biological species. One example is continuous aerosol monitoring of bacterial and other pathogens that could affect the health of livestock (such as the recent hoof and mouth disease outbreak).

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF THE INVENTION

Figure 1:
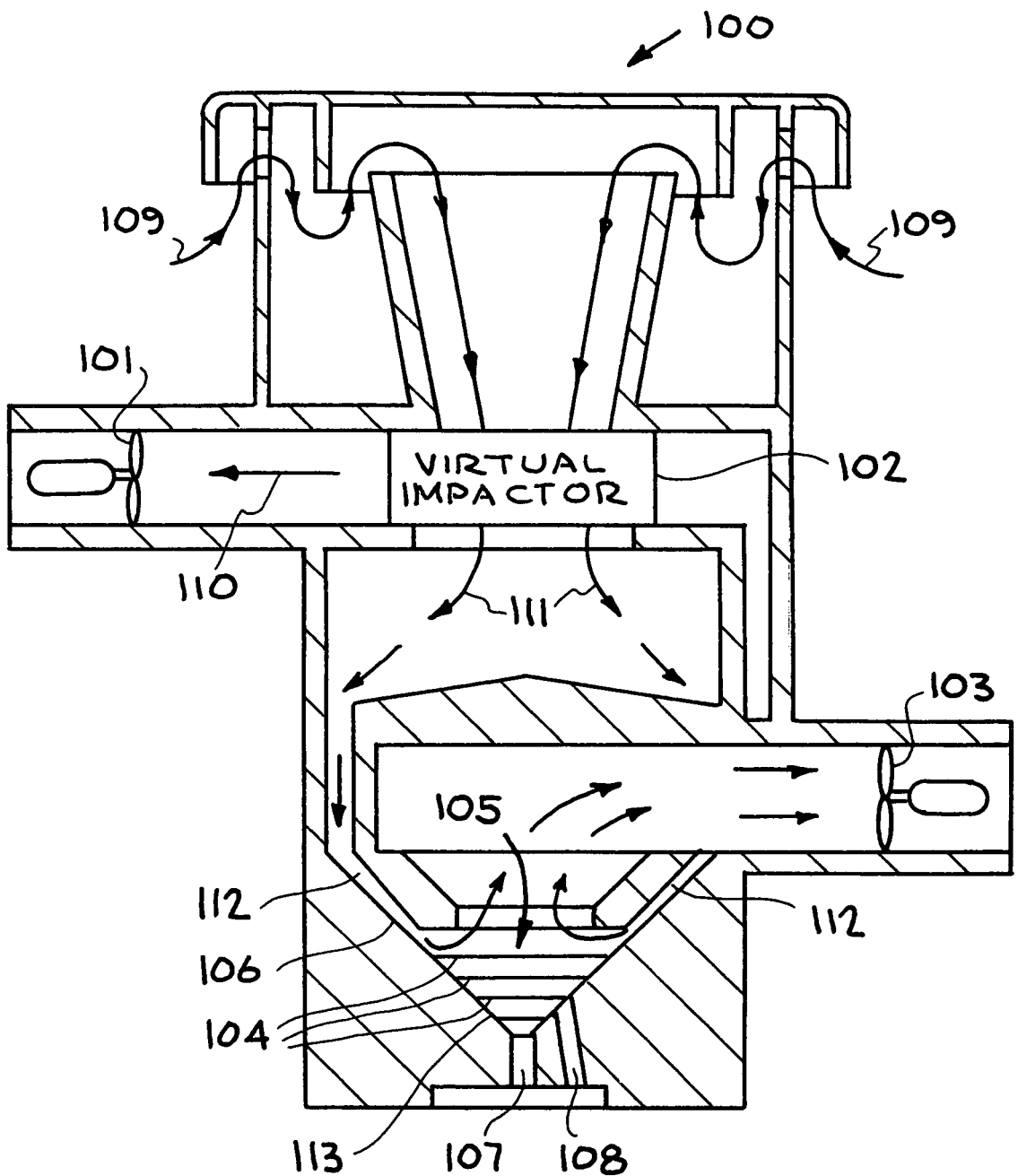
FIG. 1 illustrates an embodiment of a biobriefcase aerosol collector of the present invention.

Referring to the drawings, to the following detailed description, and to incorporated materials, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

Detection and identification of airborne contaminants and bio-hazards in the environment requires the collection and transport of particles into a liquid sample at a concentration exceeding some minimum detectable level. This is typically done with aerosol collectors, of which many types exist. Samples from aerosol collectors are concentrated into a fluid that will be processed and analyzed in a down stream detection system. Often collection systems suffer from low throughput, poor collection efficiency, and difficulty operating in dirty environmental conditions.

Referring now to the drawings, and more particularly to FIG. 1, one embodiment of a biobriefcase aerosol collector of the present invention is illustrated. This embodiment of a biobriefcase aerosol collector is designated generally by the reference numeral 100. The biobriefcase aerosol collector 100 samples the air and collects particles that potentially include bioagents entrained in the air.

The biobriefcase aerosol collector 100 includes a collector that samples the air and collects an air sample that could potentially contain bioagents entrained in the air. The collector 100 can be a collector such as that disclosed in U.S. Pat. No. 6,402,817 issued Jun. 11, 2002 to Werner Bergman or U.S. Pat. No. 6,688,187 issued Feb. 10, 2004 to Donald A. Masquelier or U.S. Pat. No. 6,520,034 issued Feb. 18, 2005 to Donald A. Masquelier et al. U.S. Pat. No. 6,402,817 issued Jun. 11, 2002, U.S. Pat. No. 6,688,187 to Donald A. Masquelier, and U.S. Pat. No. 6,520,034 to Donald A. Masquelier et al are incorporated herein by reference. An impactor separates the air sample into a first flow portion that does not contain entrained particles and a second flow portion that contains particles that potentially include bioagents. The second portion is directed to a receiving surface. Liquid is directed to the receiving surface and a liquid surface is produced. The second portion of the air sample is directed to the liquid surface so that the second portion of the air sample, with the entrained particles, impacts the liquid surface. The particles, potentially including bioagents, become captured in the liquid. A liquid output port directs the liquid and the particles, potentially including bioagents, captured in the liquid from the receiving surface for analysis.

As illustrated in FIG. 1, the biobriefcase aerosol collector 100 includes the following structural components: high flow fan 101, virtual impactor 102, low flow fan 103, contacts for fluid level control 104, fluid bowl 105, a receiving surface 106 on the fluid bowl, a sample out port 107, and a refill port 108. A cone surface 113 is positioned adjacent the receiving surface 106 of the fluid bowl 105. The cone surface 113 and the receiving surface 106 of the fluid bowl 105 produce an annulus for receiving the liquid 112. The contacts for fluid level control 104 are on the cone surface 113.

The structural components of the biobriefcase aerosol collector 100 having been described, the operation of the biobriefcase aerosol collector 100 will now be considered. As illustrated in FIG. 1 the high flow fan 101 brings air flow 109 into the biobriefcase aerosol collector 100. The virtual impactor 102 divides air flow 109 flowing into the biobriefcase aerosol collector 100 into two components. For example the virtual impactor 102 can divide air flow 109 into two components as illustrated in U.S. Pat. No. 6,402,817 and in U.S. Pat. No. 6,688,187 which are incorporated herein by reference. The first component is the major flow 110 of air less particle of interest. The second component is low flow 111 of air and concentrated particles. The low flow 111 of air and concentrated particles is directed to the fluid bowl 105.

The liquid 112 is directed to the receiving surface 106 of the fluid bowl 105. In the embodiment illustrated in FIG. 1, the liquid is water. Other liquids are used in other embodiments. The liquid 112 provides a liquid surface. The low flow 111 of air and concentrated particles is directed onto the receiving surface of the liquid 112. The open aerosol collector bowl 105 has a uniform volume of liquid 112 that is maintained by the contacts 104 for fluid level control. The bowl 105 is made of a stack of insulators and contacts that allow for a continuity measurement to be made between layers. The contacts 104 for fluid level control provide precise fluid flow and do not suffer from clogging or accumulation of debris in the collector bowl 105. Additional fluid level sensors can be used. For example the contacts 104 can be acoustic contacts or optical sensors. The volume of low flow 111 of air and concentrated particles is flowed across the bowl 105 in an annulus at a rate with sufficient velocity to entrain the particles into the liquid surface, but cause minor turbulence on the surface 113 resulting in insignificant evaporation of the liquid. This leads to low fluid loss in the system 100.

The biobriefcase aerosol collector 100 has very low fluid consumption. The contacts 104 for fluid level control prevent contamination by debris and allow for high particle concentration rates. The resulting system is a compact, robust, and economical aerosol collector for use in field portable biodetection systems. There are many uses for the biobriefcase aerosol collector 100. One is for sample collection of biohazards in transportation systems or other public environments. Another is for collection of samples for analysis of contamination in human and animal care facilities and distribution centers.

Figure 2:
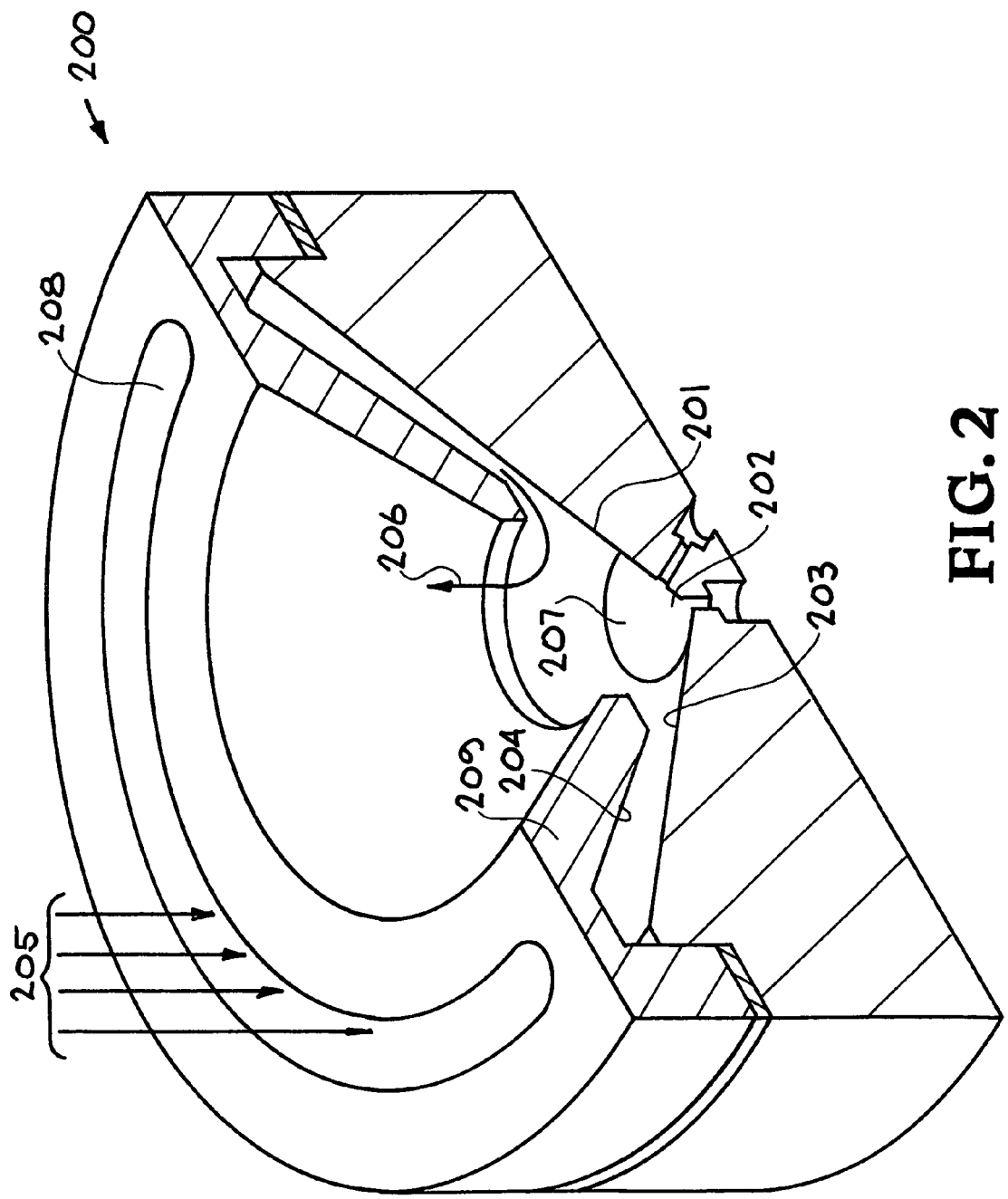
FIG. 2 illustrates another embodiment of a biobriefcase aerosol collector of the present invention.

Referring now to FIG. 2, another embodiment of a biobriefcase aerosol collector of the present invention is illustrated. This embodiment of a biobriefcase aerosol collector is designated generally by the reference numeral 200. The portion of the air sample that contains particles that potentially include bioagents is illustrated as intake air flow represented by the arrows 205. The intake air flow 205 continues through the biobriefcase aerosol collector 200 as illustrated by the arrows 206. The biobriefcase aerosol collector 200 includes structural components including a fluid bowl 201, a liquid 202, a bowl receiving surface 203, a forcing cone surface 204, and a liquid surface 207 on the liquid 202.

The intake air flow 205 comes in through an intake 208. The forcing cone surface 204 and the bowl surface 203 act together to form an air velocity increase. The velocity of the incoming air can be optimized by shimming the forcing cone 209 relative to the bowl surface 203. The shimming involves placing shims between the housing and the forcing cone 209 to move the forcing cone 209 relative to the bowl surface 203. This adjustment allows for optimization of the air volume, velocity and liquid surface disruptions.

Without the present invention, significant liquid surface disruptions result in fluid loses due to slashing than evaporation. Using the system of the present invention, the air with particles entrained in the air impacts the liquid surface with sufficient velocity to entrain the particles into the liquid but cause minor turbulence. The liquid surface has a surface tension and said the air with particles entrained in the air impacts the liquid surface with sufficient velocity to entrain the particles into said liquid, but cause minor turbulence on the surface resulting in insignificant evaporation of the liquid. This configuration allows for particle collection with low fluid lost due to splashing. The air volume 206 passes over the liquid surface 207 interacting with the surface at adequate velocity to have the particles ingrain in the liquid 202. Because this device is circular the air volume to liquid volume is very large.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A biobriefcase aerosol collector apparatus for sampling air with an air velocity, collecting particles entrained in the air wherein the particles potentially including bioagents, and capturing the particles in a liquid, comprising:
    a biobriefcase aerosol collector unit including
    a fluid bowl,
    a fluid bowl receiving surface on said fluid bowl,
    a forcing cone,
    a forcing cone surface on said forcing cone, wherein said forcing cone surface is positioned above said fluid bowl receiving surface,
    a liquid input that directs the liquid to said fluid bowl receiving surface and produces a liquid surface on the liquid,
    a fan that brings the air into said biobriefcase aerosol collector unit, and
    a virtual impactor that directs the air between said fluid bowl receiving surface and said forcing cone surface and provides an air velocity increase so that the air with particles entrained in the air impacts said liquid surface on the liquid, wherein the particles potentially including bioagents become captured in the liquid.

2. The biobriefcase aerosol collector apparatus for sampling air with an air velocity, collecting particles entrained in the air wherein the particles potentially including bioagents, and capturing the particles in a liquid of claim 1 wherein said fluid bowl receiving surface and said forcing cone surface produce and annulus for receiving the liquid.

3. The biobriefcase aerosol collector apparatus for sampling air with an air velocity, collecting particles entrained in the air wherein the particles potentially including bioagents, and capturing the particles in a liquid of claim 1 including an adjustment for moving said forcing cone surface relative to said fluid bowl receiving surface.

4. A biobriefcase aerosol collector apparatus for sampling air with an air velocity, collecting particles entrained in the air wherein the particles potentially including bioagents, and capturing the particles in a liquid, comprising:
    a biobriefcase aerosol collector unit including
    a fluid bowl,
    a fluid bowl receiving surface on said fluid bowl,
    contacts for fluid level control on said fluid bowl receiving surface,
    a forcing cone,
    a forcing cone surface on said forcing cone, wherein said forcing cone surface is positioned above said fluid bowl receiving surface,
    a liquid input that directs the liquid to said fluid bowl receiving surface and produces a liquid surface on the liquid,
    a fan that brings the air into said biobriefcase aerosol collector unit, and
    a virtual impactor that directs the air between said fluid bowl receiving surface and said forcing cone surface and provides an air velocity increase so that the air with particles entrained in the air impacts said liquid surface on the liquid, wherein the particles potentially including bioagents become captured in the liquid.

5. A biobriefcase aerosol collector apparatus for sampling air with an air velocity, collecting particles entrained in the air wherein the particles potentially including bioagents, and capturing the particles in a liquid, comprising:
    a biobriefcase aerosol collector unit including
    a fluid bowl,
    a fluid bowl receiving surface on said fluid bowl,
    a forcing cone,
    a forcing cone surface on said forcing cone, wherein said forcing cone surface is positioned above said fluid bowl receiving surface,
    a liquid input that directs the liquid to said fluid bowl receiving surface and produces a liquid surface on the liquid,
    fan that brings the air into said biobriefcase aerosol collector unit and collects an air sample that could potentially contain bioagents entrained in the air, and
    an impactor that separates the air sample into a first flow portion that does not contain entrained particles and a second flow portion that contains particles that potentially include bioagents with said second portion directed between said fluid bowl receiving surface and said forcing cone surface and providing an air velocity increase wherein said second flow portion with particles entrained in the air sample impacts said liquid surface on the liquid and the particles potentially including bioagents become captured in the liquid.

6. The biobriefcase aerosol collector apparatus for sampling air with an air velocity, collecting particles entrained in the air wherein the particles potentially including bioagents, and capturing the particles in a liquid of claim 5 including an adjustment for moving said forcing cone surface relative to said fluid bowl receiving surface.

7. A biobriefcase aerosol collector apparatus for sampling air with an air velocity, collecting particles entrained in the air wherein the particles potentially including bioagents, and capturing the particles in a liquid, comprising:
    a biobriefcase aerosol collector unit including
    a fluid bowl,
    a fluid bowl receiving surface on said fluid bowl,
    contacts for fluid level control on said fluid bowl receiving surface,
    a forcing cone,
    a forcing cone surface on said forcing cone, wherein said forcing cone surface is positioned above said fluid bowl receiving surface,
    a liquid input that directs the liquid to said fluid bowl receiving surface and produces a liquid surface on the liquid,
    a fan that brings the air into said biobriefcase aerosol collector unit and collects an air sample that could potentially contain bioagents entrained in the air, and
    an impactor that separates the air sample into a first flow portion that does not contain entrained particles and a second flow portion that contains particles that potentially include bioagents with said second portion directed between said fluid bowl receiving surface and said forcing cone surface and providing an air velocity increase wherein said second flow portion with particles entrained in the air sample impacts said liquid surface and the particles potentially including bioagents become captured in the liquid.

8. A method of sampling air with an air velocity and collecting particles entrained in the air in a biobriefcase aerosol collector, the particles potentially including bioagents, comprising the steps of:
- providing a biobriefcase aerosol collector unit,
- providing a fluid bowl in said biobriefcase aerosol collector unit,
- providing a fluid bowl receiving surface on said fluid bowl,
- providing a forcing cone in said biobriefcase aerosol collector unit,
- providing a forcing cone surface on said forcing cone,
- positioning said forcing cone surface above said fluid bowl receiving surface,
- directing a liquid between said forcing cone surface and said fluid bowl receiving surface and producing a liquid surface on the liquid,
- collecting samples of the air,
- using a virtual impactor to separate said samples of air into a first flow portion that does not contain the particles entrained in the air and a second flow portion that does contains the particles entrained in the air potentially including bioagents, and
- directing said second flow portion of the samples of air so that said second flow portion of the samples of air with particles entrained in the air is directed between said forcing cone surface and said fluid bowl receiving surface and impacts said liquid surface and providing an air velocity increase, wherein the particles potentially including bioagents become captured in said liquid.

9. The method of sampling air with an air velocity and collecting particles entrained in the air in a biobriefcase aerosol collector of claim 8 wherein said liquid is water, wherein said step of directing a liquid between said forcing cone surface and said fluid bowl receiving surface and producing a liquid surface on the liquid produces a water surface, and wherein said air with particles entrained in the air impacts said water surface and entrains the particles into said water.

10. The method of sampling air with an air velocity and collecting particles entrained in the air in a biobriefcase aerosol collector of claim 8 wherein said liquid surface has a surface tension and said collector samples the air and directs the air to said liquid surface so that the air with particles entrained in the air impacts said liquid surface with a surface tension and entrains the particles into said liquid.

* * * * *